United States Patent
Vikharankar et al.

(10) Patent No.: US 11,602,339 B2
(45) Date of Patent: Mar. 14, 2023

(54) LAPAROSCOPIC PURSE STRING SUTURE DEVICE

(71) Applicant: Covidien LP, Mansfield, MA (US)

(72) Inventors: Yogesh Kishor Vikharankar, Maharashtra (IN); Sunny Kumar, Hyderabad (IN); Arifmohamad Hamaju Mujawar, Sangli (IN)

(73) Assignee: Covidien LP, Mansfield, MA (US)

( * ) Notice: Subject to any disclaimer, the term of this patent is extended or adjusted under 35 U.S.C. 154(b) by 594 days.

(21) Appl. No.: 16/798,323

(22) Filed: Feb. 22, 2020

(65) Prior Publication Data
US 2020/0297336 A1 Sep. 24, 2020

Related U.S. Application Data

(60) Provisional application No. 62/820,890, filed on Mar. 20, 2019.

(51) Int. Cl.
*A61B 17/04* (2006.01)
*A61B 17/06* (2006.01)
(Continued)

(52) U.S. Cl.
CPC ...... *A61B 17/0401* (2013.01); *A61B 17/0482* (2013.01); *A61B 17/06166* (2013.01);
(Continued)

(58) Field of Classification Search
CPC ............ A61B 17/0401; A61B 17/0482; A61B 17/06166; A61B 2017/0409;
(Continued)

(56) References Cited

U.S. PATENT DOCUMENTS

| 5,891,159 A | 4/1999 | Sherman et al. |
| 2002/0193809 A1 | 12/2002 | Meade et al. |

(Continued)

FOREIGN PATENT DOCUMENTS

| CN | 102228385 A | 11/2011 |
| CN | 103494624 A | 1/2014 |

(Continued)

OTHER PUBLICATIONS

"Trigger Definition & Meaning." Merriam-Webster, Merriam-Webster, https://www.merriam-webster.com/dictionary/trigger. (Year: 2022).*

(Continued)

*Primary Examiner* — Kathleen S Holwerda
*Assistant Examiner* — Lauren Dubose
(74) *Attorney, Agent, or Firm* — Carter, DeLuca & Farrell LLP

(57) ABSTRACT

A suture device is utilized in forming a purse string suture during, e.g., laparoscopic end to end anastomosis procedure, to effect joining of two opposing intestinal sections. The suture device is utilized in other procedures such as, e.g., transanal total mesorectal excision (TaTME) for removal of low rectal and ultra-low rectal tumors and preservation of anal sphincters to avoid permanent stomas. In particular, the suture device is utilized in forming surgical stitches used to close an internal anal structure or to narrow a passage for performing further transanal dissection to create total mesorectal excision.

20 Claims, 4 Drawing Sheets

(51) Int. Cl.
*A61B 17/00* (2006.01)
*A61B 17/11* (2006.01)

(52) U.S. Cl.
CPC .............. *A61B 2017/00818* (2013.01); *A61B 2017/0409* (2013.01); *A61B 2017/0441* (2013.01); *A61B 2017/1142* (2013.01)

(58) Field of Classification Search
CPC .... A61B 2017/0441; A61B 2017/1142; A61B 2017/00818; A61B 17/11; A61B 2017/1132; A61B 17/1114; A61B 2017/0046; A61B 2017/0608; A61B 17/0469; A61B 2017/00663; A61B 17/062; A61B 17/0491; A61B 2017/0498; A61B 17/0057; A61B 17/12009; A61B 2017/00637; A61B 2017/06052; A61B 2017/06076; A61B 2027/1107
See application file for complete search history.

(56) References Cited

U.S. PATENT DOCUMENTS

| | | | |
|---|---|---|---|
| 2012/0029547 | A1 | 2/2012 | Shelton, IV et al. |
| 2012/0059395 | A1* | 3/2012 | Kehdy .............. A61B 17/0401 606/144 |

FOREIGN PATENT DOCUMENTS

| | | |
|---|---|---|
| CN | 103494625 B | 2/2016 |
| CN | 103610478 B | 5/2017 |
| WO | 2008147555 A2 | 12/2008 |
| WO | 2010062380 A2 | 6/2010 |
| WO | 2011112721 A1 | 9/2011 |

OTHER PUBLICATIONS

Extended European Search Report issued in European Patent Application No. 20163762.6, dated Oct. 26, 2020.

* cited by examiner

LAPAROSCOPIC PURSE STRING SUTURE DEVICE

CROSS-REFERENCE TO RELATED APPLICATION

This application claims the benefit of and priority to U.S. Provisional Patent Application No. 62/820,890 filed Mar. 20, 2019, the entire disclosure of which is incorporated by reference herein.

BACKGROUND

Technical Field

The disclosure relates to a surgical device and, more particularly, to a surgical device including a rotatable biasing member supporting a needle for forming a purse string suture.

Background of Related Art

Sutures are used in a variety of surgical applications including closing ruptured or incised tissue, soft tissue attachment, anastomosis, attachment of grafts, etc. Conventionally, suturing of ruptured or incised tissues, for example, is accomplished by the surgeon passing the sharpened tip of a curved suturing needle with a suture attached to the opposite blunt end of the needle through the incised tissue segments to be sutured such that the needle tip penetrates the tissue segments causing the needle to span the incision. The needle is then pulled through the tissue segments manually causing the attached suture to follow the curved path of the needle. Usually a knot is tied at the trailing end of the suture to anchor the first stitch. This action is performed repetitively with application of tension to the needle to pull the entire suture through the tissue segments through subsequent stitches until the entire incised segments are sutured together with a plurality of stitches.

In forming a purse string suture, purse string suture devices are utilized. The purse string suture devices include a pair of serrated tissue clamping jaws provided with teeth for clamping the tissue to be sutured therebetween. Such devices include needle passages which extend through the teeth on each jaw for receiving a needle attached to a suture to be threaded through the tissue. In use, the tissue to be sutured is clamped between the jaws and the needle is manually passed through the needle passages in both jaws to thread the suture through the tissue. Thereafter, the jaws are opened and the purse string suture is tightened and wrapped to draw the tissue together. With this type of device, a considerable amount of manual effort and dexterity is required to accomplish the purse string suturing technique. Also, in such devices, it is difficult to control the flow of tissue between the teeth because an insufficient amount of space is provided to gather the tissue clamped by the jaws.

SUMMARY

In accordance with an embodiment of the disclosure, a suture device for forming a purse string suture includes an actuation assembly and an end effector operatively coupled with the actuation assembly. The end effector includes a rotational shaft, a reload configured to be received in a tubular organ, and a clamp assembly. The reload includes a shell defining a lumen dimensioned to receive the rotational shaft, a biasing member coupled to the rotational shaft for concomitant rotation, and a needle coupled to the biasing member. The clamp assembly is movable relative to the reload to clamp the tubular organ disposed therebetween. The clamp assembly includes a wall defining a passage configured to receive the reload therein. The wall defines a cutout dimensioned to receive a portion of the tubular organ.

In an embodiment, the reload may further include a plurality of inner guides extending distally from the shell.

In another embodiment, first and second inner guides of the plurality of inner guides may diametrically oppose each other.

In yet another embodiment, at least one inner guide of the plurality of inner guides may define a groove configured to receive the needle therethrough.

In still yet another embodiment, the groove of the at least one inner guide may be defined in an inner surface of the at least one inner guide to facilitate passage of the needle during rotation of the biasing member.

In still yet another embodiment, the biasing member may be concentrically arranged with the rotational shaft.

In an embodiment, the needle may be detachably coupled with the biasing member.

In another embodiment, the needle may be attached to a radially outer-most portion of the biasing member.

In an embodiment, the clamp assembly may further include outer guides extending radially inward from the wall.

In another embodiment, the outer guides of the clamp assembly may be in registration with the inner guides of the reload.

In yet another embodiment, adjacent inner guides of the reload may define a gap therebetween.

In still yet another embodiment, the gap defined by the adjacent inner guides of the reload may be in registration with the cutout defined in the wall of the clamp assembly.

In accordance with another embodiment of the disclosure, an end effector for use with a suture device for forming a purse string suture includes a rotational shaft, a reload, and a clamp assembly. The reload includes a shell defining a lumen dimensioned to receive the rotational shaft therethrough, a biasing member having a coil coupled to the rotational shaft for concomitant rotation therewith, and a needle coupled to the biasing member. The clamp assembly includes a wall defining a passage configured to receive the reload therein. The clamp assembly is transitionable between a clamping position, in which, the reload is disposed within the passage of the clamp assembly to clamp tissue disposed between the reload and the clamp assembly, and a spaced apart position, in which, at least a portion of the reload is displaced from the passage of the clamp assembly.

In accordance with another embodiment of the disclosure, a suture device for forming a purse string suture includes a handle assembly, an elongate member, and an end effector. The handle assembly includes a trigger and a rotational knob. The elongate member is operatively coupled with the trigger for axial displacement of the elongate member. The end effector includes a rotational shaft coupled with the rotation knob for concomitant rotation therewith, a clamp assembly coupled to the elongate member such that actuation of the trigger advances the clamp assembly, and a reload configured to be received in the clamp assembly. The reload includes a shell defining a lumen, a biasing member having a coil coupled to the rotational shaft for concomitant rotation therewith, and a needle coupled to the biasing member.

In an embodiment, the suture device may further include a suture attached to the needle.

BRIEF DESCRIPTION OF THE DRAWINGS

Various embodiments of the disclosure are described hereinbelow with reference to the drawings, wherein.

DETAILED DESCRIPTION

Figure 1:
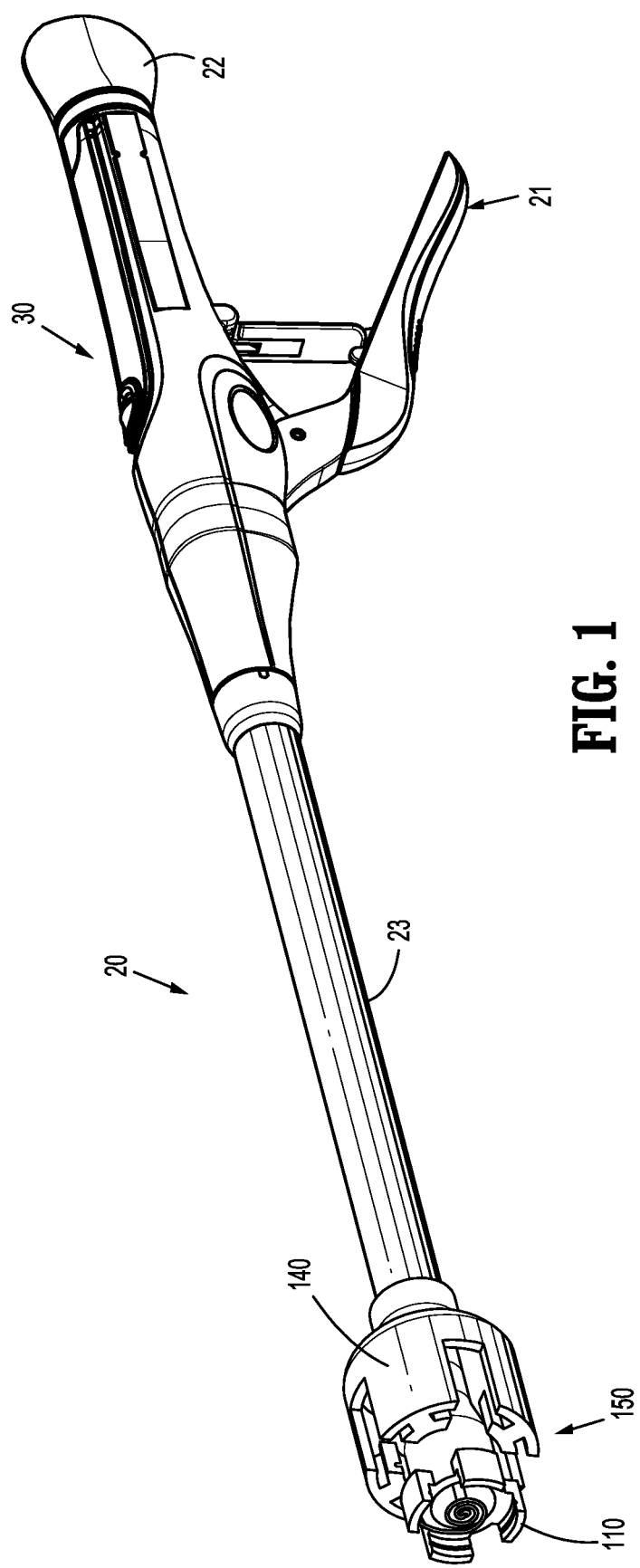
FIG. 1 is a perspective view of a suture device in accordance with an embodiment of the disclosure.

Embodiments of the disclosure will now be described in detail with reference to the drawings, in which like reference numerals designate identical or corresponding elements in each of the several views. As used herein, the term "distal," as is conventional, will refer to that portion of the instrument, apparatus, device or component thereof which is farther from the user while, the term "proximal," will refer to that portion of the instrument, apparatus, device or component thereof which is closer to the user. In the following description, well-known functions or constructions are not described in detail to avoid obscuring the disclosure in unnecessary detail.

FIG. 1 illustrates a suture device 20 configured to form a purse string suture. For example, the suture device 20 may be utilized in forming a purse string suture during, e.g., laparoscopic end to end anastomosis procedure, to effect joining of two opposing intestinal sections. The suture device 20 may be utilized in other procedures such as, e.g., transanal total mesorectal excision (TaTME) for removal of low rectal and ultra-low rectal tumors and preservation of anal sphincters to avoid permanent stomas. In particular, the suture device 20 may be utilized in forming surgical stitches used to close an internal anal structure or to narrow a passage for performing further transanal dissection to create total mesorectal excision. The suture device 20 generally includes a handle assembly 30 including a trigger 21 and a rotation knob 22, an elongate member 23 extending distally from the handle assembly 30, and an end effector 150 releasably coupled to the elongate member 23. An outer diameter of the end effector 150 and/or the elongate member 23 may be dimensioned for minimally invasive entry into an opening in tissue. The end effector 150 includes a reload 110 and a clamp assembly 140. In particular, the reload 110 may be configured for a single use, and the clamp assembly 140 may be sterilized for reuse.

Figure 2:
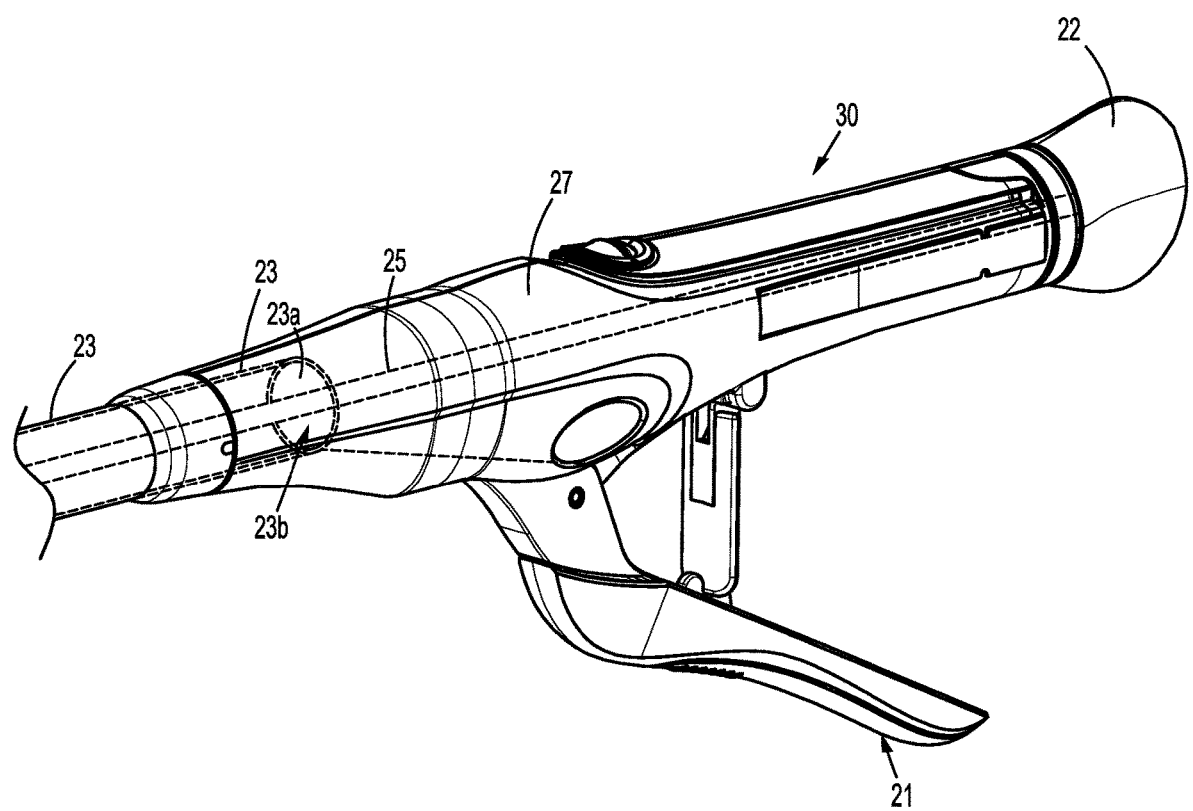
FIG. 2 is a partial perspective view of the suture device of FIG. 1, illustrating an actuation assembly in phantom.

FIG. 2 illustrates the trigger 21 of the handle assembly 30 operably coupled with the clamping assembly 140 (FIG. 1) of the end effector 150. In particular, a proximal portion 23a (shown in phantom) of the elongate member 23 extends into a housing 27 of the handle assembly 30 and is coupled to the trigger 21 such that actuation of the trigger 21 causes axial displacement of the elongate member 23. In addition, the elongate member 23 defines a lumen 23b dimensioned to receive an actuation shaft 25 (shown in phantom) therethrough. The actuation shaft 25 is operatively coupled with the rotation knob 22 of the handle assembly 30 for concomitant rotation therewith. In addition, the actuation shaft 25 is further coupled with a rotational shaft 152 (FIG. 4) of the reload 110 for concomitant rotation therewith. The rotational shaft 152 includes a proximal section (not shown) configured to engage the actuation shaft 25 of the elongate member 23 such that rotation of the rotation knob 22 of the handle assembly 30 imparts concomitant rotation to the rotational shaft 152. For example, the proximal section of the rotational shaft 152 may include a cavity (not shown) having a cross-section complementary to a cross-section of the actuation shaft 25, or vice versa, such that rotation of the actuation shaft 25 causes concomitant rotation of the rotational shaft 152. However, the actuation shaft 25 is axially fixed. Under such a configuration, the elongate member 23 and the actuation shaft 25 may be independently actuatable.

Figure 3:
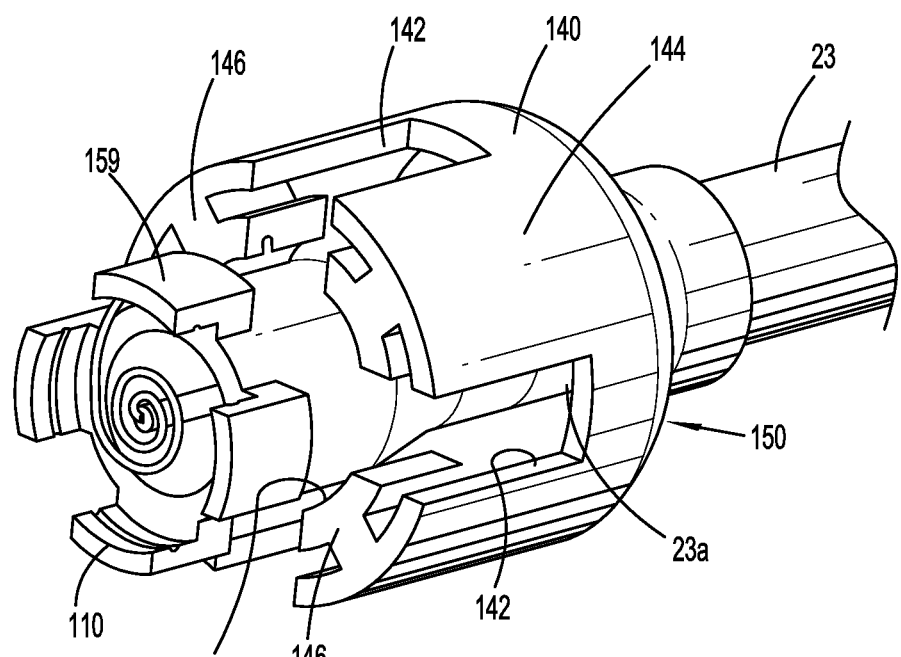
FIG. 3 is a perspective view of an end effector of the suture device of FIG. 1.

FIG. 3 illustrates the clamp assembly 140 transitionable between a clamping position, in which, the reload 110 is received within the clamp assembly 140 to clamp tissue disposed between the reload 110 and the clamp assembly 140, and a spaced apart position, in which, the reload 110 is displaced from the clamp assembly 140. The clamp assembly 140 defines a plurality of cutouts 142 circumferentially arranged thereabout. The cutouts 142 may be uniformly arranged. Each cutout 142 may be dimensioned to receive tissue therein. The clamp assembly 140 includes walls 144. Adjacent walls 144 define a cutout 142. The clamp assembly 140 further includes a plurality of outer guides 146. The outer guides 146 extend radially inward from respective walls 144. Each outer guide 146 includes an engaging surface 148 having an arcuate profile to support, e.g., tissue, thereagainst. In addition, the arcuate profile may conform to the contour of respective inner guides 159 of the reload 110.

Figure 4:
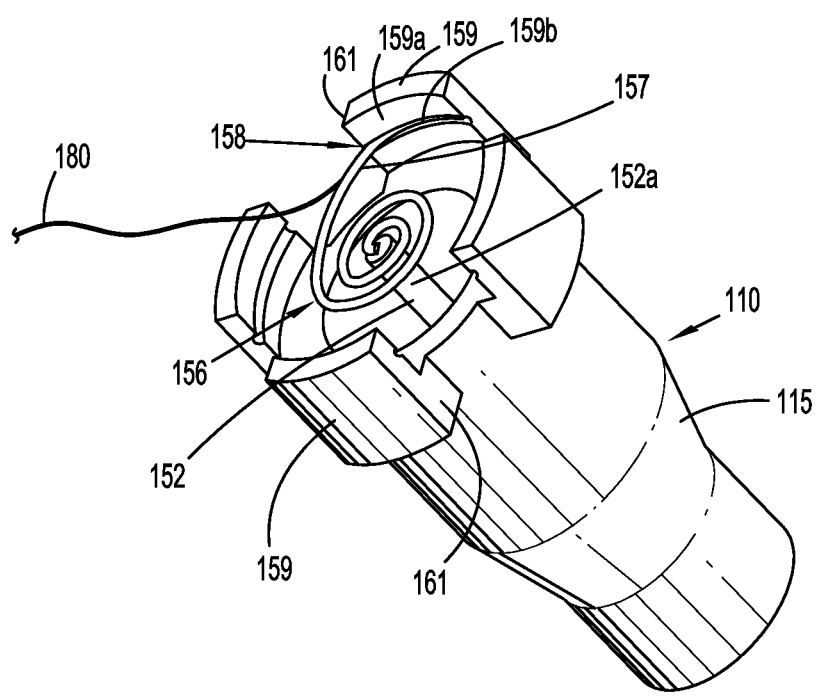
FIG. 4 is a perspective view of a reload of the end effector of FIG. 3.

FIGS. 3 and 4 illustrate the reload 110 detachably coupled to the actuation shaft 25 (FIG. 2). In particular, the rotational shaft 152 of the reload 110 is detachably coupled to the actuation shaft 25 for concomitant rotation therewith. Under such a configuration, the reload 110 may be disposable after a single use. The cavity defined in the proximal portion of the rotational shaft 152 may be circular such that the actuation shaft 25 may be attached to the rotational shaft 152 in any relative orientation. However, the cavity of the rotational shaft 152 may include a non-circular cross-section to receive the actuation shaft 25 in a predetermined orientation relative to the clamp assembly 140 such that the orientation of the reload 110 relative to the clamp assembly 140 is fixed.

The reload 110 includes a shell 115 rotatably supporting the rotational shaft 152 therein. The shell 115 is configured to slidably engage the clamp assembly 140 to enable axial displacement of the clamp assembly 140. As discussed hereinabove, the rotational shaft 152 is coupled to the actuation shaft 25 (FIG. 2) for concomitant rotation. A distal end portion 152a of the rotational shaft 152 includes a biasing member 156 such as, e.g., a torsion spring, concentrically disposed with the rotational shaft 152. The reload 110 further includes a needle 157 coupled to the biasing member 156. The needle 157 terminates in a sharp tissue penetrating point 158. The needle 157 is detachably coupled to a radially outer-most portion of the biasing member 156.

FIG. 4 illustrates the reload 110 further including inner guides 159 extending distally from the shell 115. In particular, the inner guides 159 are circumferentially arranged about the biasing member 156. The reload 110 defines a plurality of cutouts 161 such that each cutout 161 is interposed between the adjacent inner guides 159. Each cutout 161 may be dimensioned to receive tissue therein. For example, when a tubular organ is received over the reload 110, tissue may be received into the cutout 161 to facilitate formation of purse string suture. Each inner guide 159 includes an inner wall 159a defining a groove 159b dimensioned to receive the needle 157 therethrough to facilitate circular rotation of the needle 157.

The needle 157 and/or the biasing member 156 may be made from, e.g., semi-stiff implantable wire, such as titanium. Alternatively, the needle 157 and/or the biasing member 156 may include plastic or absorbable materials. Examples of materials that can be used in constructing the body may include titanium, titanium alloys, stainless steel, nickel, chrome alloys and any other biocompatible implantable metals. Alternatively, other options for materials are liquid crystal polymers, HDPE, polyglycolic acid, and polyglycolid hydroxgacetic acid. At least a portion of the needle 157 may be coated with a biocompatible lubricious material that provides for easier delivery of the needle 157 into tissue.

Figure 5:
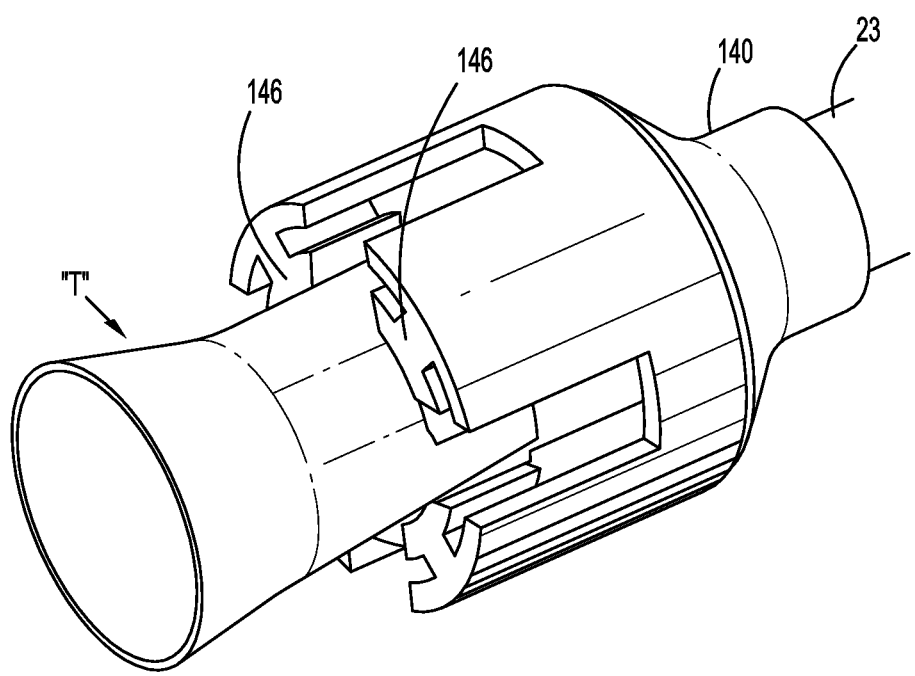
FIG. 5 is a perspective view of the end effector of FIG. 3, illustrating use with a tubular organ.
Figure 6:
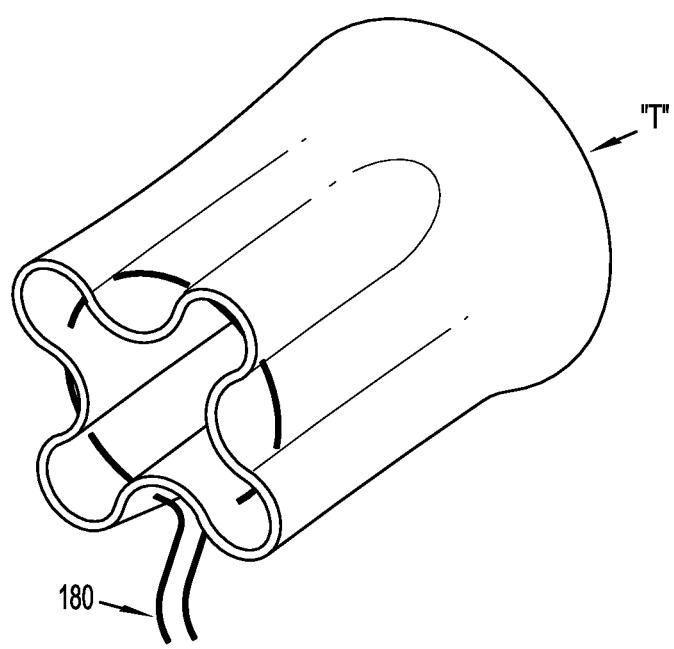
FIG. 6 is a perspective view of a tubular organ, illustrating formation of a purse string suture.

FIGS. 5 and 6 illustrate use of the suture device 20. Initially, the reload 110 is coupled with the distal portion of the actuation shaft 25 with the reload 110 in a desired orientation relative to the clamp assembly 140. For example, the reload 110 may be oriented such that when the clamp assembly 140 is in the clamping position, the cutouts 161 of the reload 110 are in registration with the cutouts 142 of the clamp assembly 140. In this manner, tissue may be received in both the cutouts 142 and the cutouts 161. Alternatively, the reload 110 may be oriented such that the inner guides 159 of the reload 110 are in registration with the respective cutouts 142 of the clamp assembly 140 when the clamp assembly 140 is in the clamping position.

Thereafter, the end effector 150 is inserted through an opening or an incision in tissue. For example, a tubular organ "T" (on which purse string suture is to be formed) is placed over the reload 110 such that the inner guides 159 of the reload 110 are disposed within the tubular organ "T". At this time, portions of the tubular organ "T" may be positioned in the cutouts 161 and/or cutouts 142. The clinician at this time may actuate the trigger 21, which, in turn, advances the clamp assembly 140 such that the outer guides 146 engage the tubular organ "T" surrounding the inner guides 159 of the reload 110. In this manner, tissue or the tubular organ "T" is secured between the reload 110 and the clamp assembly 140. At this time, the clinician may rotate the rotation knob 22 to rotate the needle 157 through the grooves 159b of the inner guide 159 and tissue or the tubular organ "T". In this manner, a purse string suture is formed. Once the purse string suture is formed, the clinician may rotate the rotation knob 22 in an opposite direction, which releases the needle 157 from the biasing member 156. At this time, the suture device 20 may be removed from the surgical site. Thereafter, the clinician may use graspers to tie the loose ends of the suture 180. In this manner, uniform needle rotation, tissue penetration and suture advancement may be obtained independent of the skill of the clinician. In addition, formation of a purse string suture is simplified by, e.g., eliminating the need for complicated maneuvering of a needle inside, e.g., an anal canal, which may further reduce injuries to tissue.

Although the illustrative embodiments of the disclosure have been described herein with reference to the accompanying drawings, the above description, disclosure, and figures should not be construed as limiting, but merely as exemplifications of particular embodiments. For example, while a mechanically triggered actuation assembly has been shown, it is also envisioned that a powered actuation utilizing a motor may be utilized to provide rotational output to the rotational shaft 152 of the end effector 150 and axial displacement to the elongate member 23. In addition, it is further contemplated that the suture device 20 may be adapted for use in robotic surgery.

It is also to be appreciated that the disclosure may be utilized in a number of applications including ligating tissue, hernia mesh repair, and in conjunction with implant drug delivery systems or procedures involving positioning of surgical or implantable devices in patients. It is to be understood, therefore, that the disclosure is not limited to those precise embodiments, and that various other changes and modifications may be effected therein by one skilled in the art without departing from the scope or spirit of the disclosure.

What is claimed is:

1. A suture device for forming a purse string suture comprising:
   an actuation assembly; and
   an end effector operatively coupled with the actuation assembly, the end effector including:
      a rotational shaft;
      a reload configured to be received in a tubular organ, the reload including:
         a shell defining a lumen dimensioned to receive the rotational shaft;
         a biasing member coupled to the rotational shaft for concomitant rotation; and
         a needle coupled to the biasing member; and
      a clamp assembly movable relative to the reload to clamp the tubular organ disposed therebetween, the clamp assembly including a wall defining a passage configured to receive the reload therein, the wall defining a cutout dimensioned to receive a portion of the tubular organ.

2. The suture device according to claim 1, wherein the reload further includes a plurality of inner guides extending distally from the shell.

3. The suture device according to claim 2, wherein first and second inner guides of the plurality of inner guides diametrically oppose each other.

4. The suture device according to claim 2, wherein at least one inner guide of the plurality of inner guides defines a groove configured to receive the needle therethrough.

5. The suture device according to claim 4, wherein the groove of the at least one inner guide is defined in an inner surface of the at least one inner guide to facilitate passage of the needle during rotation of the biasing member.

6. The suture device according to claim 1, wherein the biasing member is concentrically arranged with the rotational shaft.

7. The suture device according to claim 1, wherein the needle is detachably coupled with the biasing member.

8. The suture device according to claim 1, wherein the needle is attached to a radially outer-most portion of the biasing member.

9. The suture device according to claim 2, wherein the clamp assembly further includes outer guides extending radially inward from the wall.

10. The suture device according to claim 9, wherein the outer guides of the clamp assembly are in registration with the plurality of inner guides of the reload.

11. The suture device according to claim 9, wherein adjacent inner guides of the reload define a gap therebetween.

12. The suture device according to claim 11, wherein the gap defined by the adjacent inner guides of the reload is in registration with the cutout defined in the wall of the clamp assembly.

13. An end effector for use with a suture device for forming a purse string suture, comprising:
   a rotational shaft;
   a reload including:
      a shell defining a lumen dimensioned to receive the rotational shaft therethrough;
      a biasing member having a coil coupled to the rotational shaft for concomitant rotation therewith; and
      a needle coupled to the biasing member; and
   a clamp assembly including a wall defining a passage configured to receive the reload therein, wherein the clamp assembly is transitionable between a clamping position, in which, the reload is disposed within the passage of the clamp assembly to clamp tissue disposed between the reload and the clamp assembly, and a spaced apart position, in which, at least a portion of the reload is displaced from the passage of the clamp assembly.

14. The end effector according to claim 13, wherein the reload further includes a plurality of inner guides extending distally from the shell.

15. The end effector according to claim 14, wherein the plurality of inner guides are disposed distal of the clamp assembly when the clamp assembly is in the spaced apart position.

16. The end effector according to claim 15, wherein the clamp assembly further includes outer guides extending radially inward from the wall.

17. The end effector according to claim 16, wherein the plurality of inner guides of the reload are in registration with the respective outer guides of the clamp assembly when the clamp assembly is in the clamping position.

18. A suture device for forming a purse string suture, comprising:
   a handle assembly including:
      a trigger; and
      a rotational knob;
   an elongate member operatively coupled with the trigger for axial displacement of the elongate member; and
   an end effector including:
      a rotational shaft coupled with the rotational knob for concomitant rotation therewith;
      a clamp assembly coupled to the elongate member such that actuation of the trigger advances the clamp assembly; and
      a reload configured to be received in the clamp assembly, the reload including:
         a shell defining a lumen;
         a biasing member having a coil coupled to the rotational shaft for concomitant rotation therewith; and
         a needle coupled to the biasing member.

19. The suture device according to claim 18, further comprising a suture attached to the needle.

20. The suture device according to claim 18, wherein the clamp assembly is transitionable between a clamp position, in which, the reload is disposed within the clamp assembly such that tissue disposed between the reload and the clamp assembly is clamped therebetween, and a spaced apart position, in which, at least a portion of the reload is disposed distal of the clamp assembly.

* * * * *